United States Patent
Kimura et al.

(10) Patent No.: US 7,049,464 B2
(45) Date of Patent: May 23, 2006

(54) PROCESS FOR PRODUCING OF AN AMINOALKYLSULFONIC ACID AND A METHOD OF SALT EXCHANGE FOR A SALT THEREOF

(75) Inventors: Takuhiro Kimura, Kawagoe (JP); Tsutomu Tani, Kawagoe (JP); Reiji Miyahara, Yokohama (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/526,438

(22) PCT Filed: Aug. 27, 2003

(86) PCT No.: PCT/JP03/10859

§ 371 (c)(1),
(2), (4) Date: Mar. 3, 2005

(87) PCT Pub. No.: WO2004/035531

PCT Pub. Date: Apr. 29, 2004

(65) Prior Publication Data

US 2005/0261370 A1     Nov. 24, 2005

(30) Foreign Application Priority Data

Sep. 6, 2002   (JP)   .............................. 2002-261630

(51) Int. Cl.
*C07C 309/14*   (2006.01)
(52) U.S. Cl. ..................................................... 562/104
(58) Field of Classification Search ................. 562/104
See application file for complete search history.

(56) References Cited

U.S. PATENT DOCUMENTS 4,657,704 A    4/1987   Yamamoto et al. ..... 260/513 B

FOREIGN PATENT DOCUMENTS

| DE | 1 122 540 | 1/1962 |
|----|-----------|--------|
| JP | 40-23007 | 10/1965 |
| JP | 46-2087 | 1/1971 |
| JP | 47-16807 | 5/1972 |
| JP | 57-26654 | 2/1982 |
| JP | 60-23360 A | 2/1985 |
| JP | 4-149168 | 5/1992 |
| JP | 4-154756 A | 5/1992 |
| JP | 6-345717 A | 12/1994 |
| WO | 84/00958 A1 | 3/1984 |
| WO | 01/26832 A1 | 4/2001 |

OTHER PUBLICATIONS

Goldberg, Alan A., "Taurine", *J. Chem. Soc.*, (1943), pp. 4-5.
Cortese, Frank, "On the Synthesis of Taurine", *J. Am. Chem. Soc.*, (1936), pp. 191-192.
Schick, John W. et al., "Synthesis of Taurine and N-Methyltaurine", *Industrial and Engineering Chemistry*, vol. 39, No. 7, 1947, pp. 906-909.

*Primary Examiner*—Peter O'Sullivan
(74) *Attorney, Agent, or Firm*—Kubovcik & Kubovcik

(57) ABSTRACT

A process for producing an aminoalkylsulfonic acid of formula [2]:

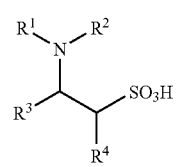

[2]

wherein $R^1$ and $R^2$ are each independently hydrogen, alkyl, aryl or aralkyl; and $R^3$ and $R^4$ are each independently hydrogen or alkyl, comprising reacting an aminoalkylsulfonate salt of formula [1]:

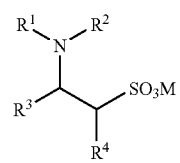

[1]

wherein M is alkali metal, organic ammonium or ammonium ion; and $R^1$ to $R^4$ are as described above, an aqueous solution thereof, or a solution dissolving any one of them in a water-soluble organic solvent, selected from alcohols having 1 to 3 carbon, carboxylic acids having 2 to 12 carbon and dimethylformamide, with an organic acid; and a method of salt exchange for an aminoalkylsulfonate salt of formula [1']:

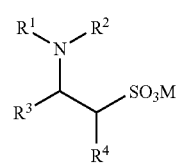

[1']

wherein M' is alkali metal, organic ammonium or ammonium ion; and $R^1$ and $R^4$ are as described above, comprising reacting the aminoalkylsulfonate salt formula [2] with a hydroxide of formula [6]:

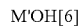

wherein M' is as described above, in alcohol or water.

27 Claims, No Drawings

PROCESS FOR PRODUCING OF AN AMINOALKYLSULFONIC ACID AND A METHOD OF SALT EXCHANGE FOR A SALT THEREOF

This application is a 371 of international application PCT/JP2003/010859, which claims priority based on Japanese patent application No. 2002-261630 filed Sept. 6, 2002, which is incorporated herein by reference.

BACKGROUND OF THE INVENTION

1. Technical Field

The present invention relates to a process for efficiently producing an aminoalkylsulfonic acid in an industrial scale, and a method of salt exchange for an aminoalkylsulfonate salt.

2. Prior Art

Aminoalkylsulfonic acids are useful compounds as intermediate raw materials such as skin cleansing agents consisting of soap and shampoo, surfactants and pH buffers, and drug raw materials.

Further, since aminoalkylsulfonic acids are amphoteric compounds having a strongly acidic functional group together with an amine group, it is expected that a fatty acid soap having different properties can be prepared by neutralizing a fatty acid with taurine or N-methyltaurine, which are a type of said compound, together with a strong alkali such as sodium hydroxide, to form a counterion bond between a carboxyl group of the fatty acid and an amine group of the amphoteric compound.

As a method for producing aminoalkylsulfonic acids, the following methods are known; for example, (1) a method for reacting ethyleneimine, sulfurous acid gas and water [see, e.g. JP-B-40-23007 (p. 1), JP-B-47-16807 (p. 1), etc.], (2) a method for heating N-methylaminoethane sulfate salt at 120–210° C. [see, e.g. JP-B-46-2087 (p. 1)], (3) a method for oxidation of 2,2-disubstituted thiazolidine with hydrogen peroxide, followed by hydrolysis [see, e.g. JP-A-57-26654 (p. 1–2)], (4) a method for reacting 2-aminoethanol sulfate ester with sodium sulfite [see, e.g. Journal of the Chemical Society, p. 4 (1943)], (5) a method for reacting a hydrogen halide salt of 2-halogenoethylamine with a sulfite salt [see, e.g. Journal of the American Chemical Society, Vol. 58, p. 191 (1936)], (6) a method for reacting a sulfite salt in an aqueous solution heated at temperature not lower than 50° C. with a halogenated alkylamine [see, e.g. WO 84/00958 (p. 5 and 20), JP-A-60-23360 (p. 1 and 3), JP-A-4-149168 (p. 1–3), etc.].

However, these methods have the following problems. Namely, the method (1) has problems such as difficult to control of reaction temperature due to generation of an extremely exothermic reaction; low yield due to side reactions such as polymerization of ethyleneimine; and difficult to handle to ethyleneimine and sulfurous acid gas as starting materials in an industrial scale due to toxicities. The method (2) has a problem of difficult to handle production in an industrial scale due to a reaction at high temperature. The method (3) has problems such as use of hydrogen peroxide which is difficult-to-handle in view of safety; and complicated operations requiring recovery and reuse of ketone type as by-products. The method (4) has problems such as heating for long period due to extremely slow reaction of sulfate esters with sodium sulfite, thereby resulting in low yield due to production of ethanolamine as a by-product by hydrolysis of sulfate esters during the reaction; difficult to separate and recovery monoethanolamine as a by-product.

Further, the method (5) and (6) have a problem of difficult to separate and recovery sulfite salts required to be used in excess amount.

Furthermore, the following methods are known as methods for producing an aminoalkylsulfonic acid from an aminoalkylsulfate salt: for example, (I) a method for reacting ammonium aminoethanesulfonate with hydrogen chloride, followed by extracting resulting aminoethanesulfonic acid with 95% ethanol and cooling the ethanol aqueous solution to precipitate an objective compound [see, e.g. Industrial and Engineering Chemistry, Vol. 39, P. 906 (1947)]; and (II) a method for reacting an aqueous solution of sodium aminoethanesulfonate with a mineral acid such as sulfuric acid and hydrogen chloride, followed by concentrating the resulting aqueous solution of aminoethanesulfonic acid to crystallize a part of sodium chloride as impurities at high temperature not lower than 80° C., and dilute the mother liquid with water and cooling to obtain an objective compound as crystal [see, e.g. DE 1122540 (p. 3–4 and 13), JP-A-6-345717 (p. 2–4) etc.].

However, the method (I) has problems such as an undesirable industrial process due to a large amount of ethanol to be used for extraction; repeated operations of the extraction to obtain high purity product; complicated treatment to be required for separating ammonium hydrochloride as impurities which is contained in almost the same amount to an objective compound; and undesirable disposal of the impurity in view of environmental conservation. In addition, the method (II) has problems such as complicated operations to be required for difficult to separate inorganic substances such as sodium chloride as impurities and a water-soluble aminoalkylsulfonic acid in an aqueous solution; and repeated operations to be required for recovery of filtrate and crystallization because an object compound can be crystallized only partly by this method.

Under such circumstances, development of a method for efficiently producing a high purity aminoalkylsulfonic acid in an industrial scale is required.

SUMMARY OF THE INVENTION

The present invention has been completed under such circumstances mentioned above, and the theme of the invention is to provide a process for efficiently producing an aminoalkylsulfonic acid in an industrial scale.

The present invention has been made to solve the problems mentioned above, and provides the following;

(1) a process for producing an aminoalkylsulfonic acid represented by the general formula [2]:

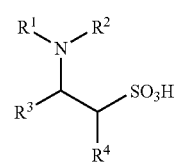

[2]

wherein $R^1$ and $R^2$ are each independently a hydrogen atom, an alkyl group, an aryl group or an aralkyl group; and $R^3$ and $R^4$ are each independently a hydrogen atom or an alkyl group, comprising reacting an aminoalkylsulfonate salt represented by the general formula [1]:

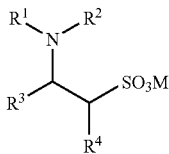

wherein M is an alkali metal atom, an organic ammonium ion or an ammonium ion; and $R^1$ to $R^4$ are the same as described above, aqueous solution thereof, or a solution dissolving any one of them in a water-soluble organic solvent, selected from alcohols having 1 to 3 carbon atoms, carboxylic acids having 2 to 12 carbon atoms and dimethylformamide, with an organic acid; and (2) a method of salt exchange for an aminoalkylsulfonate salt represented by the general formula [1']:

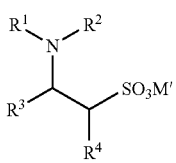

wherein M' is an alkali metal atom, an organic ammonium ion or an ammonium ion; and $R^1$ to $R^4$ are the same as described above, comprising reacting an aminoalkylsulfonate salt represented by the general formula [1]:

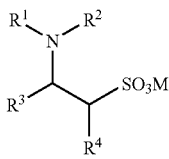

wherein $R^1$ to $R^4$ and M are the same as described above, an aqueous solution thereof, or a solution dissolving any one them in a water-soluble organic solvent, selected from alcohols having 1 to 3 carbon atoms, carboxylic acids having 2 to 12 carbon atoms and dimethylformamide, with an organic acid to obtain an aminoalkylsulfonic acid represented by the general formula [2]:

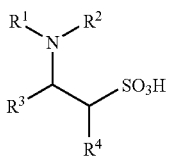

wherein $R^1$ to $R^4$ are the same as described above, and,
reacting the resulting aminoalkylsulfonic acid with a hydroxide represented by the general formula [6]:

M'OH     [6]

wherein M' is the same as described above, in an alcohol or water.

Namely, the present inventors have conducted extensive study to attain the objectives mentioned above to arrive at the findings that the aminoalkylsulfonic acid represented by the general formula [2] can be efficiently produced and easily obtained in crystal form, by reacting an aminoalkylsulfonate salt represented by the general formula [1], an aqueous solution thereof, or a solution dissolving any one of them in a water-soluble organic solvent, selected from alcohols having 1 to 3 carbon atoms, carboxylic acids having 2 to 12 carbon atoms and dimethylformamide, with an organic acid, and further that the aminoalkylsulfonate salt represented by the general formula [1] can be converted efficiently to an aminoalkylsulfonate salt having an objective salt type (M'), represented by the general formula [1'], by reacting thus obtained aminoalkylsulfonic acid with a hydroxide represented by the general formula [6], in an alcohol or water, and thus completed the present invention.

In the general formulae [1] and [2], an alkyl group represented by $R^1$ and $R^2$ may be straight chained, branched or cyclic group, and includes one having generally 1 to 12 carbon atoms, preferably 1 to 6 carbon atoms and more preferably 1 to 3 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, etc., and among others, a methyl group is preferable.

The aryl group represented by $R^1$ and $R^2$ includes one having generally 6 to 10 carbon atoms, which is specifically exemplified by a phenyl group, a naphthyl group and the like, and among others, a phenyl group is preferable.

The aralkyl group represented by $R^1$ and $R^2$ includes one having generally 7 to 9 carbon atoms, which is specifically exemplified by, for example, a benzyl group, a phenethyl group and a phenylpropyl group, and among others, a benzyl group is preferable.

The alkyl group represented by $R^3$ and $R^4$ may be straight chained, branched or cyclic group, and includes one having generally 1 to 6 carbon atoms and preferably 1 to 3 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a cyclopropyl group, a cyclobutyl group, a cyclopentyl group, a cyclohexyl group, etc., and among others, a methyl group is preferable.

In the general formulae [1], [1'] and [6], the alkali metal atom represented by M and M' includes, for example, a lithium atom, a sodium atom, a potassium atom and a rubidium atom, and among others, a preferable one includes a sodium atom and a potassium atom, and a more preferable one includes a sodium atom.

The organic ammonium ion represented by M and M' includes, for example, a monoethanolammonium ion, a diethanolammonium ion, a triethanolammonium ion, a 1,3-dihydroxy-2-methyl-2-propylammonium ion, etc., and among others, a triethanolammonium ion is preferable.

The preferable specific examples of the aminoalkylsulfonate salt represented by the general formula [1] include, for example, alkali metal salts of taurine, N-methyltaurine, N-ethyltaurine, etc. (e.g. a lithium salt, a sodium salt, a potassium salt, a rubidium salt, a cesium salt, etc.), organic ammonium salts of taurine, N-methyltaurine, N-ethyltaurine, etc. (e.g. a monoethanolammonium salt, a diethanolammonium salt, a triethanolammonium salt, a 1,3-dihydroxy-2-methyl-2-propylammonium salt, etc.), ammonium salts of taurine, N-methyltaurine, N-ethyltaurine, etc., and among others, a preferable one includes an alkali metal salt of aminoalkylsulfonic acid, and a more preferable one includes a taurine sodium salt, an N-methyltaurine sodium salt and an N-ethyltaurine sodium salt.

The preferable specific examples of the aminoalkylsulfonic acid represented by the general formula [2] include, for example, taurine, N-methyltaurine, N-ethyltaurine, etc., and among others, N-methyltaurine is preferable.

The organic acid includes, for example, a carboxylic acid and a sulfonic acid.

The carboxylic acid as the organic acid includes, for example, a monocarboxylic acid having 1 to 12 carbon atoms and a dicarboxylic acid having 2 to 12 carbon atoms.

The sulfonic acid as the organic acid includes one having 1 to 12 carbon atoms.

The monocarboxylic acid having 1 to 12 carbon atoms includes, for example, one represented by the general formula [3]:

$$R^5-COOH \qquad [3]$$

wherein $R^5$ is a hydrogen atom, or an alkyl group, an alkenyl group, an aryl group or an aralkyl group, which may have a substituent.

The dicarboxylic acid having 2 to 12 carbon atoms includes, for example, one represented by the general formula [4]:

$$HOOC-R^6-COOH \qquad [4]$$

wherein $R^6$ is an alkylene group, an alkenylene group, an arylene group or an aralkylene group, which may have a substituent.

The sulfonic acid having 1 to 12 carbon atoms includes one represented by the general formula [5]:

$$R^7-SO_3H \qquad [5]$$

wherein $R^7$ is an alkyl group, an aryl group or an aralkyl group, which may have a substituent.

In the general formula [3], the alkyl group of the alkyl group which may have a substituent, represented by $R^5$ may be straight chained, branched or cyclic group, and includes one having generally 1 to 11 carbon atoms, preferably 1 to 5 carbon atoms and more preferably 1 to 3 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, etc., and among others, for example, a methyl group and an ethyl group are preferable.

The alkenyl group of the alkenyl group which may have a substituent, represented by $R^5$ may be straight chained, branched or cyclic group, and includes one having generally 1 to 11 carbon atoms, preferably 1 to 6 carbon atoms and more preferably 1 to 3 carbon atoms, which is specifically exemplified by, for example, a vinyl group, an allyl group, a 1-propenyl group, an isopropenyl group, a 3-butenyl group, a 2-butenyl group, a 1-butenyl group, a 1,3-butadienyl group, a 4-pentenyl group, a 3-pentenyl group, a 2-pentenyl group, a 1-pentenyl group, a 1,3-pentadienyl group, a 2,4-pentadienyl group, a 1,1-dimethyl-2-propenyl group, a 1-ethyl-2-propenyl group, a 1,2-dimethyl-1-propenyl group, a 1-methyl-1-butenyl group, a 5-hexenyl group, a 4-hexenyl group, a 3-hexenyl group, a 2-hexenyl group, a 1-hexenyl group, a 1-methyl-1-hexenyl group, a 2-methyl-2-hexenyl group, a 3-methyl-1,3-hexadienyl group, a 1-heptenyl group, a 2-octenyl group, a 3-nonenyl group, a 4-decenyl group, a 1-undecenyl group, a 1-cyclopropenyl group, 2-cyclopentenyl group, a 2,4-cyclopentadienyl group, a 1-cyclohexenyl group, a 2-cyclohexenyl group, a 3-cyclohexenyl group, a 2-cycloheptenyl group, a 2-cyclononenyl group, a 3-cyclododecenyl group, etc.

The aryl group of the aryl group which may have a substituent, represented by $R^5$ includes one having generally 6 to 10 carbon atoms, which is specifically exemplified by, for example, a phenyl group, a naphthyl group and the like, and among others, a phenyl group is preferable.

The aralkyl group of the aralkyl group which may have a substituent, represented by $R^5$ includes one having generally 7 to 11 carbon atoms and preferably 7 to 9 carbon atoms, which is specifically exemplified by, for example, a benzyl group, a phenethyl group, a phenylpropyl group, a phenylbutyl group, a phenylpentyl group, etc.

In the general formula [4], the alkylene group of the alkylene group which may have a substituent, represented by $R^6$ may be straight chained, branched or cyclic group, and includes one having generally 1 to 10 carbon atoms, preferably 1 to 6 carbon atoms and more preferably 1 to 3 carbon atoms, which is specifically exemplified by, for example, straight chained alkylene groups such as a methylene group, an ethylene group, a trimethylene group, a tetramethylene group, a pentamethylene group, a hexamethylene group, a heptamethylene group, an octamethylene group, a nonamethylene group, a decamethylene group, etc.; branched alkylene groups such as a propylene group, a 1-methyltrimethylene group, a 2-methyltrimethylene group, a 1-methyltetramethylene group, a 2-methyltetramethylene group, a 1,1-dimethyltrimethylene group, a 1,2-dimethyltrimethylene group, a 1,3-dimethyltrimethylene group, a 2-ethyltrimethylene group, a 1-methylpentamethylene group, a 2-methylpentamethylene group, a 3-methylpentamethylene group, a 1,2-dimethyltetramethylene, a 1,3-dimethyltetramethylene, a 2,3-dimethyltetramethylene group, a 1,1-dimethyltetramethylene group, a 1-ethyltetramethylene group, a 2-ethyltetramethylene group, a 1-ethyl-2-methyltrimethylene group, a 1-methylhexamethylene group, a 1-methylheptamethylene group, a 1-methyloctamethylene group, a 1-methylnonamethylene group, etc.; and cycloalkylene groups such as a cyclopropylene group, a cyclopentylene group, a cyclohexylene group, a cycloheptylene group, a cyclooctylene group, a cyclononylene group, a cyclodecylene group, etc.

The alkenylene group of the alkenylene group which may have a substituent, represented by $R^6$ may be straight chained, branched or cyclic group, and includes one having generally 2 to 10 carbon atoms, preferably 2 to 6 carbon atoms and more preferably 2 to 4 carbon atoms, which is specifically exemplified by, for example, a vinylene group, a propenylene group, a 1-butenylene group, a 2-butenylene group, a 1,3-butadienylene group, a 1-methylpropenylene group, a 1-methyl-2-propenylene group, a 1-pentenylene group, a 2-pentenylene group, a 1,3-pentadienylene group, a 1,4-pentadienylene group, a 1-methylbutenylene group, a 1-methyl-1,2-butadienylene group, a 1-hexenylene group, a 2-hexenylene group, a 3-hexenylene group, a 1-methylpentenylene group, a 2-methyl-2-pentenylene group, a 1,1-dimethyl-2-propenylene group, a 1-ethyl-2-propenylene group, a 1,2-dimethylpropenylene group, a 1-methyl-1-butenylene group, a 1-heptenylene group, a 1-methylhexenylene group, a 2-methyl-2-hexenylene group, 1,2-dimethylpentenylene group, a 1-octenylene group, a 2-octenylene group, a 3-nonenylene group, a 4-decenylene group, a 1-cyclopropenylene group, a 2-cyclopentenylene group, a 2,4-cyclopentadienylene group, a 1-cyclohexenylene group, a 2-cyclohexenylene group, a 1-cycloheptenylene group, a 2-cyclononenylene group, a 3-cyclodecenylene group, a 2-cyclododecenylene group, etc.

The arylene group of the arylene group which may have a substituent, represented by $R^6$ includes one having generally 6 to 10 carbon atoms, which is specifically exemplified by, for example, an o-phenylene group, a m-phenylene group, a p-phenylene group, a p-xylene-α,α'-diyl group, a naphthylene group, etc.

The aralkylene group of the aralkylene group which may have a substituent, represented by $R^6$ includes one having generally 7 to 10 carbon atoms, which is specifically exemplified by, for example, —CH$_2$—C$_6$H$_4$—, —CH$_2$—C$_6$H$_4$—CH$_2$—, —CH$_2$CH$_2$—C$_6$H$_4$—, —CH$_2$CH$_2$—C$_6$H$_4$—CH$_2$—, —CH$_2$CH$_2$CH$_2$—C$_6$H$_4$—, —CH(CH$_3$)—CH$_2$—C$_6$H$_4$—, —CH$_2$CH$_2$CH$_2$CH$_2$—C$_6$H$_4$—, —CH$_2$CH$_2$CH(CH$_3$)—C$_6$H$_4$—, etc.

In the general formula [5], the alkyl group of the alkyl group which may have a substituent, represented by $R^6$ may be straight chained, branched or cyclic group, and includes one having generally 1 to 12 carbon atoms, preferably 1 to 6 carbon atoms and more preferably 1 to 4 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, etc., and among others, a methyl group is preferable.

The aryl group of the aryl group which may have a substituent, represented by $R^7$ includes one having generally 6 to 10 carbon atoms, which is specifically exemplified by, for example, a phenyl group, a naphthyl group and the like, and among others, a phenyl group is preferable.

The aralkyl group of the aralkyl group which may have a substituent, represented by $R^7$ includes one having generally 7 to 12 carbon atoms and preferably 7 to 9 carbon atoms, which is specifically exemplified by, for example, a benzyl group, a phenethyl group, a phenylpropyl group, a phenylbutyl group, a phenylpentyl group, a phenylhexyl group, etc.

In the general formulae [3] to [5], the substituent of the alkyl group, the alkenyl group, the aryl group and the aralkyl group, which may have a substituent, represented by $R^5$, the alkylene group, the alkenylene group, the arylene group and the aralkylene group, which may have a substituent, represented by $R^6$, and the alkyl group, the aryl group and the aralkyl group, which may have a substituent, represented by $R^7$ includes, for example, halogen atoms such as a fluorine atom, a chlorine atom, a bromine atom and an iodine atom; lower alkyl groups having 1 to 4 carbon atoms such as a methyl group, an ethyl group, a n-propyl group, an isopropyl group, a n-butyl group, an isobutyl group, a sec-butyl group and a tert-butyl group; lower alkoxy groups having 1 to 4 carbon atoms such as a methoxy group, an ethoxy group, a n-propoxy group, an isopropoxy group, a n-butoxy group, an isobutoxy group, a sec-butoxy group and a tert-butoxy group; and an amino group, a nitro group, a carbonyl group, a hydroxyl group, etc.

The preferable specific examples of the monocarboxylic acid having 1 to 12 carbon atoms, represented by the general formula [3] include, for example, aliphatic saturated carboxylic acids such as formic acid, acetic acid, propionic acid, butyric acid, isobutyric acid, valeric acid, isovaleric acid, pivalic acid, hexanoic acid, heptanoic acid, octanoic acid, nonanoic acid, decanoic acid, undecanoic acid, lauric acid, etc.; alicyclic carboxylic acids such as cyclohexane carboxylic acid, etc.; halogenated alkyl carboxylic acids such as fluoroacetic acid, difluoroacetic acid, trifluoroacetic acid, trichloroacetic acid, tribromoacetic acid, triiodoacetic, acid, trifluoropropionic acid, perfluoropropionic acid, perchloropropionic acid, perbromopropionic acid, periodopropionic acid, trifluorobutyric acid, perfluorobutyric acid, perchlorobutyric acid, perbromobutyric acid, periodobutyric acid, trifluorovaleric acid, perfluorovaleric acid, perchlorovaleric acid, perbromovaleric acid, periodovaleric acid, perfluorohexanoic acid, perchlorohexanoic acid, perbromohexanoic acid, periodohexanoic acid, perfluoroheptanoic acid, perchloroheptanoic acid, perbromoheptanoic acid, periodoheptanoic acid, perfluorooctanoic acid, perchlorooctanoic acid, perbromooctanoic acid, periodooctanoic acid, perfluorononanoic acid, perchlorononanoic acid, perbromononanoic acid, periodononanoic acid, perfluorodecanoic acid, perchlorodecanoic acid, perbromodecanoic acid, periododecanoic acid, perfluoroundecanoic acid, perchloroundecanoic acid, perbromoundecanoic acid, periodoundecanoic acid, perfluorododecanoic acid, perchlorododecanoic acid, perbromododecanoic acid, periodododecanoic acid, etc; hydroxy aliphatic carboxylic acids such as glycolic acid, lactic acid, glyceric acid, 3-hydroxy-2-methylpropionic acid, etc.; aliphatic ketone carboxylic acids such as pyruvic acid, acetoacetic acid, 5-oxovaleric acid, etc.; aliphatic unsaturated carboxylic acids such as acrylic acid, methacrylic acid, crotonic acid, isocrotonic acid, 2-pentenoic acid, 3-hexenoic acid, 3-heptenoic acid, 4-octenoic acid, 4-nonenoic acid, 5-decenoic acid, 5-undecenoic acid, 6-dodecenoic acid, etc.; alicyclic carboxylic acids such as camphoric acid, adamantane carboxylic acid, etc.; aromatic carboxylic acids such as benzoic acid, naphthoic acid, etc.; alkylaromatic carboxylic acids such as toluic acid, etc.; halogenated aromatic carboxylic acids such as fluorobenzoic acid, chlorobenzoic acid, bromobenzoic acid, iodobenzoic acid, difluorobenzoic acid, dichlorobenzoic acid, dibromobenzoic acid, diiodobenzoic acid, trifluorobenzoic acid, trichlorobenzoic acid, tribromobenzoic acid, triiodobenzoic acid, tetrafluorobenzoic acid, tetrachlorobenzoic acid, tetrabromobenzoic acid, tetraiodobenzoic acid, pentafluorobenzoic acid, pentachlorobenzoic acid, pentabromobenzoic acid, pentaiodobenzoic acid, fluoronaphthoic acid, chloronaphthoic acid, bromonaphthoic acid, iodonaphthoic acid, perfluoronaphthoic acid, perchloronaphthoic acid, perbromonaphthoic acid, periodonaphthoic acid, etc.; halogenated alkyl aromatic carboxylic acids such as trifluoromethylbenzoic acid, trichloromethylbenzoic acid, tribromomethylbenzoic acid, triiodomethylbenzoic acid, bis(trifluoromethyl) benzoic acid, tris(trifluoromethyl)benzoic acid, tris (trichloromethyl)benzoic acid, tris(tribromomethyl)benzoic acid, trifluoromethylnaphtoic acid, trichloromethylnaphtoic acid, tribromomethylnaphtoic acid, triiodomethylnaphtoic acid, bis(trifluoromethyl)naphthoic acid, etc.; alkoxy aromatic carboxylic acids such as anisic acid, veratric acid, o-veratric acid, gallic acid, etc.; halogenated alkoxy aromatic carboxylic acids such as trifluoromethoxybenzoic acid, pentafluoroethoxybenzoic acid, trichloromethoxybenzoic acid, pentachloroethoxybenzoic acid, tribromomethoxybenzoic acid, pentabromoethoxybenzoic acid, triiodomethoxybenzoic acid, pentaiodoethoxybenzoic acid, etc.; nitro aromatic carboxylic acids such as trinitro benzoic acid, etc.; hydroxy aromatic carboxylic acids such as salicylic acid, o-pyrocatechuic acid, β-resorcylic acid, gentisic acid, γ-resorcylic acid, protocatechuic acid, α-resorcylic acid, etc.; hydroxy alkoxy aromatic carboxylic acids such as vanillic acid, isovanillic acid, etc.; aralkyl carboxylic acids such as α-toluic acid, hydrocinnamic acid, hydratropic acid, 3-phenylpropanoic acid, 4-phenylbutanoic acid, 5-phenylpentanoic acid, 6-phenylhexanoic acid, etc.; hydroxyl aralkyl carboxylic acids such as homogentisic acid, etc.; aromatic hydroxy alkyl carboxylic acids such as mandelic acid, benzilic acid, atrolactic acid, tropaic acid, atroglyceric acid, etc.; aliphatic ketone carboxylic acids such as pyruvic acid, acetoacetic acid, etc.; amino aromatic carboxylic acids such as anthranillic acid, etc.; amino acids such as alanine, arginine, asparagine, cysteine, glutamine, glycine, histidine, isoleucine, leucine, lysine, methionine, phenylalanine, proline, serine, threonine, tryptophan, tyrosine, valine, etc.; p-formylphenyl acetic acid, etc. and among others, a preferable one includes a lower aliphatic saturated carboxylic acid having 2 to 5 carbon atoms such as acetic acid, propionic acid and butyric acid, and a more preferable one includes acetic acid.

The preferable specific examples of the dicarboxylic acid having 2 to 12 carbon atoms, represented by the general formula [4] include, for example, saturated aliphatic dicarboxylic acids such as oxalic acid, malonic acid, succinic acid, glutaric acid, adipic acid, pimelic acid, suberic acid, azelaic acid, sebacic acid, undecanedioic acid, dodecanedioic acid, etc.; halogenated saturated aliphatic dicarboxylic acids such as difluoromalonic acid, 2,2-difluorosuccinic acid, tetrafluorosuccinic acid, hexafluoroglutaric acid, octafluoroadipic acid, dodecafluorosuberic acid, perfluoro-1,9-nonanedicarboxylic acid, perfluoro-1,10-decanedicarboxylic acid, etc.; unsaturated aliphatic dicarboxylic acids such as maleic acid, fumaric acid, citraconic acid, mesaconic acid, etc.; halogenated unsaturated aliphatic dicarboxylic acids such as 2,2-difluoromaleic acid, 2,2-difluorofumaric acid, 2,2-difluoro-3-pentenedioic acid, perfluoro-3-hexenedioic acid, etc.; hydroxyl saturated aliphatic dicarboxylic acids such as tartronic acid, malic acid, tartaric acid, etc.; aromatic dicarboxylic acids such as phthalic acid isophthalic acid, terephthalic acid, etc.; halogenated aromatic dicarboxylic acids such as 3-fluorophthalic acid, tetrafluorophthalic acid, tetrafluoroterephthalic acid, etc.; alkyl aromatic dicarboxylic acids such as 2,2-bis(3-carboxyphenyl) hexafluoropropane, 2,2-bis(4-carboxyphenyl) hexafluoropropane, etc. and among others, oxalic acid, malonic acid is preferable.

The preferable specific examples of the sulfonic acid having 1 to 12 carbon atoms, represented by the general formula [5] include, for example, alkylsulfonic acids such as methanesulfonic acid, ethanesulfonic acid, propanesulfonic acid, butanesulfonic acid, pentanesulfonic acid, hexanesulfonic acid, heptanesulfonic acid, octanesulfonic acid, nonanesulfonic acid, decanesulfonic acid, undecanesulfonic acid, dodecanesulfonic acid, etc.; cycloalkylsulfonic acids such as cyclopentanesulfonic acid, cyclohexanesulfonic acid, etc.; halogenated alkylsulfonic acids such as trifluoromethanesulfonic acid, trichloromethanesulfonic acid, tribromomethanesulfonic acid, triiodomethanesulfonic acid, trifluoroethanesulfonic acid, pentafluoroethanesulfonic acid, pentachloroethanesulfonic acid, pentabromoethanesulfonic acid, pentaiodoethanesulfonic acid, heptafluoropropanesulfonic acid, heptachloropropanesulfonic acid, heptabromopropanesulfonic acid, heptaiodopropanesulfonic acid, nonafluorobutanesulfonic acid, nonachlorobutanesulfonic acid, nonabromobutanesulfonic acid, nonaiodobutanesulfonic acid, perfluoropentanesulfonic acid, perchloropentanesulfonic acid, perbromopentanesulfonic acid, periodopentanesulfonic acid, perfluorohexanesulfonic acid, perchlorohexanesulfonic acid, perbromohexanesulfonic acid, periodohexanesulfonic acid, perfluoroheptanesulfonic acid, perchloroheptanesulfonic acid, perbromoheptanesulfonic acid, periodoheptanesulfonic acid, perfluorooctanesulfonic acid, perchlorooctanesulfonic acid, perbromooctanesulfonic acid, periodooctanesulfonic acid, perfluorononanesulfonic acid, perchlorononanesulfonic acid, perbromononanesulfonic acid, periodononanesulfonic acid, perfluorodecanesulfonic acid, perchlorodecanesulfonic acid, perbromodecanesulfonic acid, periododecanesulfonic acid, perfluoroundecanesulfonic acid, perchloroundecanesulfonic acid, perbromoundecanesulfonic acid, periodoundecanesulfonic acid, perfluorododecanesulfonic acid, perchlorododecanesulfonic acid, perbromododecanesulfonic acid, periodododecanesulfonic acid, etc.; halogenated cycloalkylsulfonic acids such as 4-fluorocyclohexanesulfonic acid, 4-chlorocyclohexanesulfonic acid, 4-bromocyclohexanesulfonic acid, 4-iodocyclohexanesulfonic acid, 2,4-difluorocyclohexanesulfonic acid, 2,4-dichlorocyclohexanesulfonic acid, 2,4-dibromocyclohexanesulfonic acid, 2,4-diiodocyclohexanesulfonic acid, 2,4,6-trifluorocyclohexanesulfonic acid, 2,4,6-trichlorocyclohexanesulfonic acid, 2,4,6-tribromocyclohexanesulfonic acid, 2,4,6-triiodocyclohexanesulfonic acid, perfluorocyclohexanesulfonic acid, perchlorocyclohexanesulfonic acid, perbromocyclohexanesulfonic acid, periodocyclohexanesulfonic acid, etc.; aromatic sulfonic acids such as benzenesulfonic acid, naphthalenesulfonic acid, etc.; alkyl aromatic sulfonic acids such as p-toluenesulfonic acid, 3,5-dimethylbenzenesulfonic acid, etc.; halogenated aromatic sulfonic acids such as 2-fluorobenzenesulfonic acid, 3-fluorobenzenesulfonic acid, 4-fluorobenzenesulfonic acid, 2-chlorobenzenesulfonic acid, 3-chlorobenzenesulfonic acid, 4-chlorobenzenesulfonic acid, 2-bromobenzenesulfonic acid, 3-bromobenzenesulfonic acid, 4-bromobenzenesulfonic acid, 2-iodobenzenesulfonic acid, 4-iodobenzenesulfonic acid, 2,4-difluorobenzenesulfonic acid, 2,6-difluorobenzenesulfonic acid, 2,4-dichlorobenzenesulfonic acid, 2,6-dichlorobenzenesulfonic acid, 2,4-dibromobenzenesulfonic acid, 2,6-dibromobenzenesulfonic acid, 2,4-diiodobenzenesulfonic acid, 2,6-diiodobenzenesulfonic acid, 2,4,6-trifluorobenzenesulfonic acid, 3,4,5-trifluorobenzenesulfonic acid, 2,4,6-trichlorobenzenesulfonic acid, 3,4,5-trichlorobenzenesulfonic acid, 2,4,6-tribromobenzenesulfonic acid, 3,4,5-tribromobenzenesulfonic acid, 2,4,6-triiodobenzenesulfonic acid, 3,4,5-triiodobenzenesulfonic acid, pentafluorobenzenesulfonic acid, pentachlorobenzenesulfonic acid, pentabromobenzenesulfonic acid, pentaiodobenzenesulfonic acid, etc.; halogenated alkyl aromatic sulfonic acids such as 2-trifluoromethylbenzenesulfonic acid, 3-trifluoromethylbenzenesulfonic acid, 4-trifluoromethylbenzenesulfonic acid, 2,6-bis(trifluoromethyl)benzenesulfonic acid, 3,5-bis(trifluoromethyl)benzenesulfonic acid, 4-trichloromethylbenzenesulfonic acid, 4-tribromomethylbenzenesulfonic acid, 4-triiodomethylbenzenesulfonic acid, etc.; aralkylsulfonic acids such as benzylsulfonic acid, phenethylsulfonic acid, phenylpropylsulfonic acid, phenylbutylsulfonic acid, phenylpentylsulfonic acid, phenylhexylsulfonic acid, etc.; halogenated aralkylsulfonic acids such as p-fluorophenylmethylsulfonic acid, p-fluorophenylethylsulfonic acid, p-fluorophenylpropylsulfonic acid, p-fluorophenylbutylsulfonic acid, etc.: bicycloalkylsulfonic acids such as camphorsulfonic acid, etc. and among others, methanesulfonic acid is preferable.

The preferable specific examples of the hydroxide represented by the general formula [6] include, for example, alkali metal hydroxides such as lithium hydroxide, sodium hydroxide, potassium hydroxide, rubidium hydroxide, etc.; organic ammonium hydroxide salts such as monoethanolammonium hydroxide, diethanolammonium hydroxide, triethanolammonium hydroxide, 1,3-dihydroxy-2-methyl-2-propylammonium hydroxide; ammonium hydroxide, etc., and among others, a preferable one includes, for example, sodium hydroxide, potassium hydroxide, triethanolammonium hydroxide and ammonium hydroxide, and a more preferable one includes, for example, sodium hydroxide, potassium hydroxide and triethanolammonium hydroxide.

The preferable specific examples of the aminoalkylsulfonate salt represented by the general formula [1'] include, for example, alkali metal salts of taurine, N-methyltaurine, N-ethyltaurine (e.g. a lithium salt, a sodium salt, a potassium salt, a rubidium salt, a cesium salt, etc.); organic ammonium salts of taurine, N-methyltaurine, N-ethyltaurine, (e.g. a monoethanol ammonium salt, a diethanol ammonium salt, a triethanol ammonium salt, a 1,3-dihydroxy-2-methyl-2-propylammonium salt, etc.); ammonium salt of taurine, N-methyltaurine, N-ethyltaurine, etc., and among others, a preferable salt includes, for example, alkali metal salts of aminoalkylsulfonic acid, organic ammonium salts of aminoalkylsulfonic acid, etc., and a more preferable salt includes, for example, taurine sodium salt, taurine potassium salt, taurine triethanolammonium salt, N-methyltaurine sodium salt, N-methyltaurine potassium salt, N-methyltaurine triethanolammonium salt, etc.

The water-soluble organic solvent to be used in production of the aminoalkylsulfonic acid represented by the general formula [2] includes one capable of dissolving the aminoalkylsulfonate salt and organic acid salts obtained as by-products and not or hardly capable of dissolving the obtained aminoalkylsulfonic acid. The specific examples of the solvent include, for example, alcohols having 1 to 3 carbon atoms such as methanol, ethanol, n-propanol, etc.; carboxylic acids having 2 to 12 carbon atoms such as acetic acid, propionic acid, butyric acid, isobutyric acid, valeric acid, isovaleric acid, pivalic acid, lauric acid, etc. and dimethylformamide, etc. and among others, a preferable one includes, for example, methanol, n-propanol, acetic acid and the like, and a more preferable one includes methanol. These solvents may be used alone or in a suitable combination of two or more kinds thereof.

Further, when the carboxylic acid having 2 to 12 carbon atoms mentioned above is used as the water-soluble organic solvent, the solvent can also be used in place of the organic acid, and further addition of other organic acid is not necessary.

The process for producing the aminosulfonic acid represented by the general formula [2], of the present invention includes, for example, (A) a process for reacting an aqueous solution of the aminoalkylsulfonate salt represented by the general formula [1] with an organic acid; (B) a process for reacting the aminoalkylsulfonate salt represented by the general formula [1], which is dissolved in the water-soluble organic solvent as described above, with an organic acid; and (C) a process for reacting an aqueous solution of the aminoalkylsulfonate salt, which is dissolved in the water-soluble organic solvent as described above, with an organic acid.

Since the aminoalkylsulfonic acid obtained by these methods precipitates as crystal, and the organic acid salt as by-product is dissolved in a reaction solvent, the resulting crystal is recovered by filtration to obtain easily an objective aminoalkylsulfonic acid.

Further, when said aminoalkylsulfonic acid is produced in an industrial scale, the above methods (B) and (C) are preferable. However, the aminoalkylsulfonate salt represented by the general formula [1] as the starting material is available more easily in aqueous solution form, therefore, when such a solution is used, the method (C) is more preferable.

The aminoalkylsulfonate salt represented by the general formula [1] or an aqueous solution thereof may be a commercially available product or one synthesized suitably in accordance with a common method.

When said aminoalkylsulfonate salt is used in aqueous solution form, less water content is preferable in case of obtaining an object product in higher yield, and such amount of water content as not to be solidified is preferable in case of conducting the reaction in an industrial scale. Specifically, water content is generally 5 to 80%, and preferably 10 to 30%, relative to said aminoalkylsulfonate salt.

An amount of the water-soluble organic solvent to be used in production of an aminoalkylsulfonic acid represented by the general formula [2] depends on kinds of the aminoalkylsulfonate salt represented by the general formula [1] to be used, and generally 0.5 to 20 times by weight, and preferably 1 to 5 times by weight, relative to said aminoalkylsulfonate salt.

When the water-soluble organic solvent are mixed with water, total amount of the water-soluble organic solvent and water is generally 0.5 to 30 times by weight, and preferably 1 to 10 times by weight, relative to the aminoalkylsulfonate salt represented by the general formula [1] to be used.

An amount of the organic acid to be used depends on each kinds of said aminoalkylsulfonate salt and a solvent, to be used, and generally 0.5 to 10 times by mole, and preferably 0.8 to 2 times by mole, relative to said aminoalkylsulfonate salt.

Reaction temperature is not especially limited, and generally 0 to 200° C., preferably 0 to 110° C., and more preferably 20 to 50° C. Further, reaction temperature may be raised by applying pressure to the reaction system with inert gas such as helium gas, nitrogen gas and argon gas. In this case, pressure to be applied is, even if applying too high pressure, is not effective to improve reaction efficiency, and generally 1 to 100 $kg/cm^2$, and preferably 2 to 10 $kg/cm^2$.

Reaction time depends on reaction conditions such as reaction temperature, kinds of said aminoalkylsulfonate salt to be used, each amount of the organic solvent and the organic acid to be used, and concentrations of these substances, and generally 5 minutes to 5 hours.

Further, the aminoalkylsulfonic acid represented by the general formula [2], obtained by the method for production of the present invention can further be reacted with the hydroxide represented by the general formula [6], in alcohol or water, to produce the aminoalkylsulfonate salt represented by the general formula [1'], the salt of which has been exchanged to an objective salt (including the case when M in the general formula [1] and M' in the general formula [6] are same).

Namely, the method of salt exchange of the present invention can be used for a purification process of the aminoalkylsulfonate salt represented by the general formula [1], when M in the general formula [1] and M' in the general formula [1'] are same, while the method can also be used for a purification process and a salt exchange process, of the aminoalkylsulfonate salt represented by the general formula [1], when said M and M' are different from each other.

The alcohol to be used in reaction with the hydroxide represented by the general formula [6] includes, for example, methanol, ethanol, glycerin, etc.

An amount of the solvent to be used in this reaction depends on kinds of the aminoalkylsulfonic acid to be used, represented by the general formula [2], and generally 0.5 to 30 times by weight, and preferably 1 to 10 times by weight, relative to said aminoalkylsulfonic acid.

An amount of the hydroxide to be used, represented by the general formula [6] depends on each kinds of said aminoalkylsulfonic acid and the solvent, and generally 0.5 to 10 times by mole, and preferably 0.8 to 1.2 times by mole, relative to said aminoalkylsulfonic acid.

Further, in order to obtain the aminoalkylsulfonate salt represented by the general formula [1'] in high purity, it is desirable to be reacted with equimolar ratio of the hydroxide represented by the general formula [6], relative to said aminoalkylsulfonic acid.

Reaction temperature is not especially limited, and generally 0 to 100° C., and preferably 20 to 50° C.

Reaction time depends on the reaction conditions such as reaction temperature, kinds of said aminoalkylsulfonic acid to be used, amount of the organic solvent to be used, and concentrations of these substances, and generally 5 minutes to 5 hours.

Post-treatment after the reaction may be conducted in accordance with common methods generally conducted in this field.

The method of salt exchange for the aminoalkylsulfonate salt represented by the general formula [1'], of the present invention can be used, for example, as a purification process for the aminoalkylsulfonate salt represented by the general formula [1] or an aqueous solution thereof as starting material. Thus, the aminoalkylsulfonate salt (e.g. a sodium salt) can be obtained in high purity as aqueous solution form or crystal thereof by obtaining the aminoalkylsulfonic acid as crystal from said aminoalkylsulfonate salt (a sodium salt) or an aqueous solution thereof according to the method for production of the present invention, followed by reacting with a hydroxide derived from corresponding salt (in this case, sodium hydroxide).

Furthermore, if the aminoalkylsulfonate salt (e.g. a sodium salt) is converted to the aminoalkylsulfonic acid according to the method of production of the present invention, and then treated with a hydroxide derived from a salt different from that of the starting material (e.g. potassium hydroxide), the aminoalkylsulfonate salt having salt type different from that of the starting material (in this case, potassium salt) can be produced.

Thus, by using the method for producing the aminoalkylsulfonic acid of the present invention and further conducting salt exchange reaction of the aminoalkylsulfonate salt, the aminoalkylsulfonate salts having various objective salt types can easily be produced from the sodium aminoalkylsulfonates which can be available comparatively easily and are cheap.

The method for producing the aminoalkylsulfonic acid of the present invention can efficiently produce the aminoalkylsulfonic acid using cheap reagents, without having such problems accompanied with conventional method as difficult handling due to use of toxic ethyleneimine or sulfurous acid gas, necessity of expensive equipment due to conducting reaction of alkylamines in heated and pressurized condition and necessity of use of hydrogen peroxide which is difficult to handle in view of safety.

Further, conventional methods generate by-products such as ketones, ammonium hydrochlorides and monoethanolamine, which make it difficult to separate an objective aminoalkylsulfonic acid. On the contrary, in the method of production of the present invention, since the organic acid salt as by-products are soluble in the reaction solvent, an objective aminoalkylsulfonic acid can easily be obtained as precipitate in high purity without impurities.

In the following, the present invention is explained in detail referring to Examples, but the present invention is not limited thereto by any means.

EXAMPLES

Example 1

Synthesis of N-methyltaurine

In a stainless autoclave were prepared 100.0 g (192 mmol) of a 25% sodium vinylsulfonate aqueous solution and 16.4 g (211 mmol) of a 40% methylamine aqueous solution, and the mixture was reacted with stirring at 100±5° C. for 3 hours. After completion of the reaction, water was concentrated under reduced pressure, and 120 ml of methanol and 12.1 g (201 mmol) of acetic acid were added thereto, followed by reacting at 20 to 30° C. for 1 hour. After completion of the reaction, the reaction solution was cooled to −10° C., followed by stirring at the same temperature for 1 hour, followed by filtering crystal and drying under reduced pressure to give 22.7 g of N-methyltaurine as white crystal (yield 85%).

[Results of $^1$H-NMR analysis: Purity of not lower than 99% and sodium acetate content of not higher than 0.5%]

Example 2

Synthesis of N-methyltaurine

The same procedure as in Example 1 was conducted except for reacting at 25±5° C. for 170 hours with stirring to give 22.0 g of N-methyltaurine (yield 82%).

Example 3

Synthesis of N-methyltaurine 17.0 kg (54.9 mol) of a 52% N-methyltaurine sodium salt aqueous solution (Trade Name: NMT50 from LEUNA Co. Ltd.) was prepared and water was concentrated under reduced pressure, and then 33 L of methanol was added thereto, and 3.6 kg (60.0 mol) of acetic acid was added dropwise thereto, followed by reacting under stirring at 20 to 30° C. for 1 hour. After completion of the reaction, the reaction solution was cooled to −10° C., followed by stirring at the same temperature for 1 hour, filtering crystal and drying under reduced pressure to give 7.4 kg of N-methyltaurine as white crystal (yield 97%).

[Results of $^1$H-NMR analysis: Purity of not lower than 99% and sodium acetate content of not higher than 0.5%]

Example 4

Synthesis of N-methyltaurine

The same procedure as in Example 3 was conducted except for using propionic acid instead of acetic acid to give 7.3 kg of N-methyltaurine (yield 95%).

[Results of $^1$H-NMR analysis: Purity of not lower than 98% and sodium propionate content of not higher than 1.0%]

Example 5

A Salt Exchange Reaction from a Sodium Salt to a Potassium Salt

In an aqueous solution of 3.0 kg (53.2 mol) of potassium hydroxide and 8.4 kg of water was dissolved 7.4 kg (53.2 mol) of N-methyltaurine obtained in Example 3, and the mixture was reacted under stirring at 25 to 30° C. for 1 hour to give 18.8 kg of a 50% aqueous solution of N-methyltaurine potassium salt.

Example 6

A Salt Exchange Reaction from a Sodium Salt to an Ammonium Salt

The same procedure as in Example 5 was conducted except for using 3.6 kg (53.2 mol) of a 25% aqueous ammonia solution instead of 3.0 kg (53.2 mol) of potassium hydroxide to give 19.4 kg of a 43% aqueous solution of N-methyltaurine ammonium salt.

Example 7

A Salt Exchange Reaction from a Sodium Salt to a Triethanolammonium Salt

The same procedure as in Example 5 was conducted except for using 7.9 kg (53.2 mol) of triethanolamine instead of 3.0 kg (53.2 mol) of potassium hydroxide to give 23.7 kg of a 60% aqueous solution of N-methyltaurine triethanolammonium salt.

INDUSTRIAL APPLICABILITY

A method for producing an aminoalkylsulfonic acid of the present invention is one, wherein an alkali metal salt of an aminoalkylsulfonic acid, aqueous solution thereof, or a solution dissolving any one of them in a water-soluble organic solvent is reacted with an organic acid, which can efficiently produce an aminoalkylsulfonic acid in high purity in an industrial scale, without any such problems accompanied with conventional methods as necessity of use of toxic or substance which is difficult-to-handle in view of safety and difficult to separate an objective aminoalkylsulfonic acid from by-products thereof.

What is claimed is:

1. A process for producing an aminoalkylsulfonic acid represented by the general formula [2]:

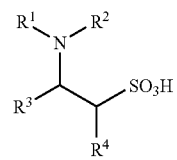

[2]

wherein $R^1$ and $R^2$ are each independently a hydrogen atom, an alkyl group, an aryl group or an aralkyl group; and $R^3$ and $R^4$ are each independently a hydrogen atom or an alkyl group, comprising reacting an aminoalkylsulfonate salt represented by the general formula [1]:

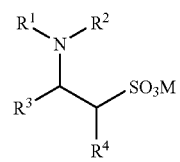

[1]

wherein M is an alkali metal atom, an organic ammonium ion or an ammonium ion; and $R^1$ to $R^4$ are the same as described above, an aqueous solution thereof, or a solution dissolving any one of them in a water-soluble organic solvent, selected from alcohols having 1 to 3 carbon atoms, carboxylic acids having 2 to 12 carbon atoms and dimethylformamide, with an organic acid.

2. The process according to claim 1, wherein the organic acid is a monocarboxylic acid having 1 to 12 carbon atoms or a dicarboxylic acid having 2 to 12 carbon atoms.

3. The process according to claim 1, wherein the organic acid is acetic acid.

4. The process according to claim 1, wherein the alcohol having 1 to 3 carbon atoms as the water-soluble organic solvent is methanol.

5. The process according to claim 1, wherein the carboxylic acid having 2 to 12 carbon atoms as the water-soluble organic solvent is acetic acid.

6. The process according to claim 1, wherein the water-soluble organic solvent is methanol.

7. The process according to claim 1, wherein $R^1$ is an alkyl group and $R^2$ to $R^4$ are each a hydrogen atom.

8. The process according to claim 1, wherein the alkali metal atom represented by M is a sodium atom.

9. The process according to claim 1, wherein the organic ammonium ion represented by M is a triethanolammonium ion.

10. The process according to claim 1, wherein M is a sodium atom.

11. The process according to claim 1, wherein the aminoalkylsulfonate salt represented by the general formula [1] is N-methyltaurine sodium salt, and the aminoalkylsulfonic acid represented by the general formula [2] is N-methyltaurine.

12. A method of salt exchange for an aminoalkylsulfonate salt represented by the general formula [1']:

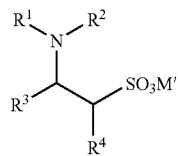

[1']

wherein $R^1$ and $R^2$ are each independently a hydrogen atom, an alkyl group, an aryl group or an aralkyl group; $R^3$ and $R^4$ are each independently a hydrogen atom or an alkyl group; and M' is an alkali metal atom, an organic ammonium ion or an ammonium ion, comprising reacting an aminoalkylsulfonate salt represented by the general formula [1]:

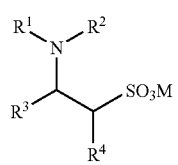

[1]

wherein M is an alkali metal atom, an organic ammonium ion or an ammonium ion; and $R^1$ to $R^4$ are the same as described above, an aqueous solution thereof, or a solution dissolving any one, them in a water-soluble organic solvent, selected from alcohols having 1 to 3 carbon atoms, carboxylic acids having 2 to 12 carbon atoms and dimethylformamide, with an organic acid to obtain an aminoalkylsulfonic acid represented by the general formula [2]:

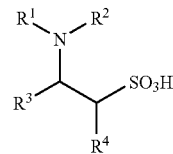

[2]

wherein $R^1$ to $R^4$ are the same as described above, and, reacting the resulting an aminoalkylsulfonic acid with a hydroxide represented by the general formula [6]:

M'OH  [6]

wherein M' is the same as described above, in an alcohol or water.

13. The method according to claim 12, wherein the organic acid is a monocarboxylic acid having 1 to 12 carbon atoms or a dicarboxylic acid having 2 to 12 carbon atoms.

14. The method according to claim 12, wherein the organic acid is acetic acid.

15. The method according to claim 12, wherein the alcohol having 1 to 3 carbon atoms as the water-soluble organic solvent is methanol.

16. The method according to claim 12, wherein the carboxylic acid having 2 to 12 carbon atoms as the water-soluble organic solvent is acetic acid.

17. The method according to claim 12, wherein the water-soluble organic solvent is methanol.

18. The method according to claim 12, wherein the alcohol used for the salt exchange reaction is ethanol.

19. The method according to claim 12, wherein $R^1$ is an alkyl group and $R^2$ to $R^4$ are each a hydrogen atom.

20. The method according to claim 12, wherein the alkali metal atom represented by M is a sodium atom.

21. The method according to claim 12, wherein the organic ammonium ion represented by M is a triethanolammonium ion.

22. The method according to claim 12, wherein M is a sodium atom.

23. The method according to claim 12, wherein the alkali metal atom represented by M' is a sodium atom or a potassium atom.

24. The method according to claim 12, wherein the organic ammonium ion represented by M' is a triethanolammonium ion.

25. The method according to claim 12, wherein the aminoalkylsulfonate salt represented by the general formula [1] is N-methyltaurine sodium salt, the aminoalkylsulfonic acid represented by the general formula [2] is N-methyltaurine, the aminoalkylsulfonate salt represented by the general formula [1'] is N-methyltaurine sodium salt, N-methyltaurine potassium salt or N-methyltaurine triethanolammonium salt.

26. The method according to claim 22, wherein the alkali metal atom represented by M' is a sodium atom or a potassium atom.

27. The method according to claim 22, wherein the organic ammonium ion represented by M' is a triethanolammonium ion.

* * * * *

UNITED STATES PATENT AND TRADEMARK OFFICE
CERTIFICATE OF CORRECTION

PATENT NO. : 7,049,464 B2
APPLICATION NO. : 10/526438
DATED : May 23, 2006
INVENTOR(S) : Takuhiro Kimura, Tsutomu Tani and Reiji Miyahara It is certified that error appears in the above-identified patent and that said Letters Patent is hereby corrected as shown below:

On the cover page, Item (54), & Col. 1 lines 1 - 4 "PROCESS FOR PRODUCING OF AN AMINOALKYLSULFONIC ACID AND A METHOD OF SALT EXCHANGE FOR A SALT THEREOF" should be --PROCESS FOR PRODUCING AN AMINOALKYLSULFONIC ACID AND A METHOD OF SALT EXCHANGE FOR A SALT THEREOF--.

In Column 17, line 57, "any one, them" should be --any one of them--.

Signed and Sealed this

Nineteenth Day of December, 2006

JON W. DUDAS
*Director of the United States Patent and Trademark Office*